(12) United States Patent
Honda et al.

(10) Patent No.: US 6,555,385 B1
(45) Date of Patent: Apr. 29, 2003

(54) SAMPLING BOTTLE FOR CHLORINATED ORGANIC COMPOUNDS

(75) Inventors: Katsuhisa Honda, Matsuyama (JP); Noriaki Hamada, Matsuyama (JP); Masazumi Yamashita, Matsuyama (JP); Hirofumi Nakamura, Matsuyama (JP); Osamu Kajikawa, Osaka (JP); Mamoru Hatada, Osaka (JP); Susumu Fujita, Osaka (JP); Atsumi Matsumoto, Osaka (JP); Tominori Sato, Osaka (JP)

(73) Assignees: Miura Co., Ltd., Ehime (JP); Osaka Gas Co., Ltd., Osaka (JP)

( * ) Notice: Subject to any disclaimer, the term of this patent is extended or adjusted under 35 U.S.C. 154(b) by 0 days.

(21) Appl. No.: 09/380,383

(22) PCT Filed: Jan. 18, 1999

(86) PCT No.: PCT/JP99/00147
§ 371 (c)(1), (2), (4) Date: Sep. 1, 1999

(87) PCT Pub. No.: WO99/37987
PCT Pub. Date: Jul. 29, 1999

(30) Foreign Application Priority Data

Jan. 23, 1998 (JP) .......................... 10-026475
Jul. 17, 1998 (JP) .......................... 10-203472

(51) Int. Cl.[7] ................................ G01N 1/18

(52) U.S. Cl. .................. 436/178; 436/124; 436/177; 436/181; 422/83; 422/88; 422/99; 422/101; 73/31.03; 73/31.07; 73/863.21

(58) Field of Search .............................. 422/83, 88, 99, 422/101, 102, 939, 940, 946, 947; 436/124, 125, 177, 178, 180, 181; 73/31.03, 31.07, 863.21, 863.23, 863.71

(56) References Cited

U.S. PATENT DOCUMENTS 4,350,502 A * 9/1982 Spatola ..................... 95/142
4,502,396 A * 3/1985 Teller ....................... 588/209

(List continued on next page.)

FOREIGN PATENT DOCUMENTS

CN  86 1 04962 A   2/1987
JP  63247639       10/1988

(List continued on next page.)

OTHER PUBLICATIONS

Ballschmiter et al. *Chemosphere*, vol. 13, No. 10, pp. 1139–1142, 1984.*
Marti et al. *Chemosphere*, vol. 25, Nos. 7–10, pp. 1349–1354, 1992.*

(List continued on next page.)

Primary Examiner—Maureen M. Wallenhorst
(74) Attorney, Agent, or Firm—Birch, Stewart, Kolasch & Birch, LLP (57) ABSTRACT

A collector is provided which is capable of simultaneously capturing and collecting particulate and gaseous chlorinated organic compounds contained in a fluid. The collector 3 includes a housing 6 and a captor 7 disposed within the housing 6. The captor 7 includes a tubular porous core member 7a of a sintered glass having one end closed with a close member 7c, and a gas-permeable sheet 7b fitted around the core member 7a. The gas-permeable sheet 7b is, for example, a paper-like sheet having a fibrous activated carbon and inorganic fibers. The particulate and gaseous chlorinated organic compounds contained in a gas sample flowing into the captor through a sampling tube 2 are simultaneously collected and removed from the gas sample by the core member 7a and the gas-permeable sheet 7b, and the gas sample free from the chlorinated organic compounds is then discharged from an outlet port 6b.

24 Claims, 5 Drawing Sheets

U.S. PATENT DOCUMENTS

| | | | | |
|---|---|---|---|---|
| 4,889,698 A | * | 12/1989 | Moller et al. | 423/210 |
| 5,439,508 A | * | 8/1995 | Mayer-Schwinning et al. | 95/58 |
| 5,493,923 A | * | 2/1996 | Balfanz et al. | 73/863.21 |

FOREIGN PATENT DOCUMENTS

| | | |
|---|---|---|
| JP | 4109139 | 4/1992 |
| JP | 4216461 | 8/1992 |
| JP | 8266863 | 10/1996 |

OTHER PUBLICATIONS

Microfilm of the specification and drawings annexed to the request of Japanese Utility Model Application No. 62–70810 (Laid–Open No. 63–181859) (Mitsubishi Electric Corp.) Nov. 24, 1988.

Manual of Standard Measurement and Analysis of Dioxins in Refuse Dump, Ministry of Health and Welfare, Japan, Mar. 1997.

Title 40, Part 60, Appendix A, Method 23, of the Code of Federal Regulations, U.S. Environmental Protection Agency (EPA), Dec. 1990.

British Standard, Stationary Source Emissions—Determination of the mass concentration of PCDDs/PCDFs, Part 1. Sampling, 1997.

British Standard, Stationary Source Emissions—Determination of the mass concentration of PCDDs/PCDFs, Part 2. Extraction and clean–up, 1997.

British Standard, Stationary Source Emissions—Determination of the mass concentration of PCDDs/PCDFs, Part 3. Identification and quantification, 1997.

* cited by examiner

SAMPLING BOTTLE FOR CHLORINATED ORGANIC COMPOUNDS

This application is the national phase under 35 U.S.C. §371 of PCT International Application No. PCT/JP99/00147 which has an International filing date of Jan. 18, 1999 which designated the United States of America.

TECHNICAL FIELD

The present invention relates to a chlorinated organic compound collector and, particularly, to a collector for collecting chlorinated organic compounds contained in a fluid.

BACKGROUND ART

Chlorinated organic compounds such as dioxins, polychlorobiphenyl (PCB), chlorophenol and chlorobenzene are generally contained in exhaust gas emitted from incineration plants for incineration of waste such as industrial waste and domestic refuse.

The term "dioxins" is herein a generic term for polychlorinated dibenzo-para-dioxins (PCDDs), polychlorinated dibenzofurans (PCDFs) and the like, which are well known as highly toxic environmental pollutants. Among these, tetrachlorodibenzodioxins ($T_4CDDs$) are known to be the most toxic. On the other hand, chlorinated organic compounds such as polychlorobiphenyl, chlorophenol and chlorobenzene are less toxic than dioxins. However, it has been found that these chlorinated organic compounds are liable to be converted into dioxins in a temperature range of the exhaust gas under certain conditions in an incinerator, for example, with various elements in flyash serving as a catalyst, so that these chlorinated organic compounds are recognized as environmental pollutants like dioxins. From the viewpoint of environmental preservation, it is imperative to establish a method of removing the aforesaid various chlorinated organic compounds from a fluid such as exhaust gas or waste water and, at the same time, efforts are being made urgently on a worldwide scale to establish a method of analyzing the chlorinated organic compounds contained in the fluid.

When the chlorinated organic compounds present in the fluid are to be analyzed, it is necessary to first obtain a sample from the target fluid in a precise and accurate manner. For the analysis of the chlorinated organic compounds present in an exhaust gas, for example, it is necessary to take a predetermined amount of a gas sample from a space such as a flue through which the exhaust gas is flowing, and assuredly capture the entire amount of the various chlorinated organic compounds contained in the gas sample. In particular, the aforesaid dioxins as the environmental pollutants are contained in a very small amount in the gas sample, and include various kinds of dioxins which are present in various forms such as particulate and gaseous forms. Therefore, a highly reliable result cannot be expected from the analysis without precise sampling. For this reason, Japan, the United States and European countries have been making attempts to formulate official guidelines for methods of taking a sample containing chlorinated organic compounds such as dioxins to ensure the accuracy of the result of the analysis.

In Japan, for example, the Ministry of Health and Welfare has formulated an official guideline, which specifies a sampling device for taking a gas sample containing chlorinated organic compounds such as dioxins. The sampling device principally comprises: a sampling tube for taking a gas sample, for example, from a flue through which an exhaust gas from an incinerator flows; a first captor including a filtering material for mainly capturing a particulate component of the chlorinated organic compounds contained in the gas sample taken through the sampling tube; and a second captor for capturing a gaseous component of the chlorinated organic compounds uncaptured by the first captor. The second captor principally comprises a liquid captor portion including a plurality of glass impingers each retaining therein an absorbent liquid, and a resin adsorbent portion including a resin adsorbent, whereby the gaseous component of the chlorinated organic compounds uncaptured by the first captor is captured by the absorbent liquid in the impingers and the resin adsorbent.

In most cases, the sampling device is repeatedly used, because the device is expensive with a complicated construction including the first captor and the second captor and with many glass components incorporated therein. Since the components, such as the impingers, of the sampling device should be kept clean to ensure the reliability of measurement data, preparatory operations such as a cleaning operation to be performed prior to the gas sampling are very troublesome. In addition, when the gaseous component of the chlorinated organic compounds contained in the gas sample is captured by the second captor, the second captor should be cooled by a coolant such as dry ice. Therefore, a sampling operation per se is very troublesome. Further, the chlorinated organic compounds captured by the first captor and the second captor are extracted after the gas sampling. At this time, the respective components of the chlorinated organic compounds captured by the first captor and the second captor should separately be extracted. This makes the extracting operation troublesome. In addition, the technique of the extracting operation often influences the reliability of the result of the analysis. Moreover, the sampling device has difficulties in handing at the gas sampling and transportation, because the sampling device inevitably has a larger size with the two kinds of captors, i.e., the first captor and the second captor, and is vulnerable to damage with many glass components.

On the other hand, the U.S. Environmental Protection Agency (EPA) and the Comite Europeen de Normalisation (CEN) have also formulated their own official guidelines. Sampling devices specified in these guidelines have substantially the same drawbacks in the complexity of the device construction and the handling difficulty with some minor differences from the sampling device specified in the Japanese guideline.

It is an object of the present invention to simultaneously capture particulate and gaseous chlorinated organic compounds contained in a fluid for collection thereof.

DISCLOSURE OF THE INVENTION

A chlorinated organic compound collector according to the present invention is intended for collecting chlorinated organic compounds contained in a fluid. The collector comprises: a vessel which permits passage of a fluid therethrough; and a captor disposed within the vessel for simultaneously capturing particulate and gaseous chlorinated organic compounds contained in the fluid for removal thereof from the fluid. The captor includes, for example, an adsorbent capable of adsorbing the chlorinated organic compounds.

In accordance with a first embodiment, the captor for use in the collector includes, for example, a gas-permeable tube having a closed end, and a gas-permeable sheet fitted around the gas-permeable tube, wherein the gas-permeable sheet includes an adsorbent capable of adsorbing the chlorinated organic compounds. The gas-permeable tube is, for example, a porous tube. The gas-permeable sheet is, for example, a paper-like sheet comprising the adsorbent and inorganic fibers, and may be in a felt form or in a laminate form.

In accordance with a second embodiment, the captor for use in the collector is, for example, a hollow cylindrical member which is formed from a gas-permeable paper-like sheet comprising inorganic fibers and an adsorbent capable of adsorbing the chlorinated organic compounds and has a closed end. In accordance with a third embodiment, the captor is, for example, a gas-permeable hollow cylindrical molded member which comprises inorganic fibers and an adsorbent capable of adsorbing the chlorinated organic compounds and has a closed end.

The adsorbent for use in the collector of the invention is, for example, an activated carbon. The activated carbon is, for example, at least one of a granular activated carbon and a fibrous activated carbon. The activated carbon has a specific surface area of 50 to 4,000 $m^2/g$, for example. In this case, the activated carbon is present, for example, in an amount of 0.1 to 4.0 g in the captor.

When the chlorinated organic compounds contained in the fluid are to be collected with the use of the chlorinated organic compound collector according to the present invention, the fluid is allowed to pass through the vessel. At this time, the fluid passes through the captor disposed within the vessel, and the particulate and gaseous chlorinated organic compounds contained in the fluid are simultaneously captured by the captor for removal thereof. As a result, the particulate and gaseous chlorinated organic compounds in the fluid are collected by the captor.

With the captor according to the first embodiment, the fluid flowing into the vessel passes through the captor, and is then discharged out of the vessel. At this time, the fluid passes through the gas-permeable tube and gas-permeable sheet of the captor in this order, whereby the particulate and gaseous chlorinated organic compounds are removed by the gas-permeable tube and the adsorbent contained in the gas-permeable sheet. That is, the particulate and gaseous chlorinated organic compounds are collected and removed from the fluid by the captor.

With the captor according to the second embodiment, the fluid flowing in to the vessel passes from the inside to the outside of the gas-permeable paper-like sheet of the captor, and is then discharged out of the vessel. At this time, the particulate and gaseous chlorinated organic compounds contained in the fluid are removed by the inorganic fibers and the adsorbent constituting the gas-permeable paper-like sheet. That is, the particulate and gaseous chlorinated organic compounds are collected and removed from the fluid by the captor.

With the captor according to the third embodiment, the fluid flowing into the vessel passes from the inside to the outside of the hollow cylindrical molded member of the captor, and is then discharged out of the vessel. At this time, the particulate and gaseous chlorinated organic compounds contained in the fluid are removed by the inorganic fibers and the adsorbent constituting the hollow cylindrical molded member. That is, the particulate and gaseous chlorinated organic compounds are collected and removed from the fluid by the captor.

Where the adsorbent for use in the captor is an activated carbon, the chlorinated organic compounds can assuredly be captured and removed from the fluid by the activated carbon, which has a particularly excellent adsorption property with respect to the chlorinated organic compounds. Where the activated carbon has a specific surface area of the aforesaid range, the activated carbon exhibits a further excellent adsorption property with respect to the gaseous chlorinated organic compounds, so that the chlorinated organic compounds in the fluid can further assuredly be captured and removed from the fluid. In this case, where the activated carbon is contained in an amount of the aforesaid range in the captor, the chlorinated organic compounds collected by the captor can easily be extracted in a short time in accordance with an inexpensive and simple extraction method with a general versatility by using a high speed extractor or a Soxhlet extractor.

Since the chlorinated organic compound collector according to the present invention includes the captor which is capable of simultaneously capturing the particulate and gaseous chlorinated organic compounds, the collector has a simpler construction and is easier to handle than the conventional collector. Therefore, the chlorinated organic compounds contained in the fluid can quickly, easily and assuredly be collected with the use of the collector. In addition, the extracting operation for extracting the chlorinated organic compounds collected by the collector is remarkably simplified as compared with a case where the conventional collector is used.

On the other hand, a chlorinated organic compound sampling method according to the present invention is intended for collecting chlorinated organic compounds contained in a fluid. The method comprises the step of simultaneously capturing particulate and gaseous chlorinated organic compounds contained in the fluid for removal thereof from the fluid.

Since the sampling method merely includes the step of simultaneously capturing the particulate and gaseous chlorinated organic compounds contained in the fluid for removal thereof from the fluid, a sampling operation for collecting the chlorinated organic compounds can be simplified as compared with the conventional method in which the particulate and gaseous components of the chlorinated organic compounds are separately collected. As a result, the sampling operation can easily be performed.

Other objects and effects of the present invention will become apparent from the following detailed description.

DETAILED DESCRIPTION OF THE INVENTION

Figure 1:
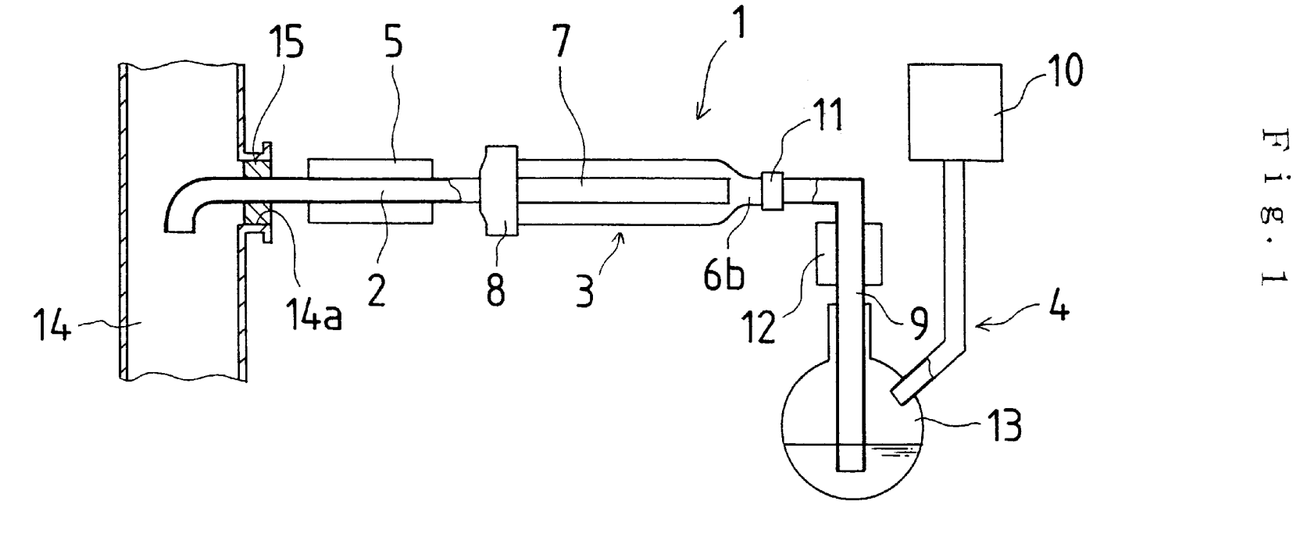
FIG. 1 is a schematic diagram illustrating a sampling device which employs a collector according to one embodiment of the present invention.

FIG. 1 schematically illustrates the construction of a chlorinated organic compound sampling device which employs a collector according to one embodiment of the present invention. The sampling device 1 is intended for collecting chlorinated organic compounds contained in a gas sample such as of an exhaust gas. In the figure, the sampling device 1 principally includes a sampling tube 2, a collector 3 (according to the embodiment of the invention), and a sucker 4.

The sampling tube 2 is, for example, a glass tube which is provided with a cooler 5 for cooling a gas sample flowing through the tube.

Figure 2:
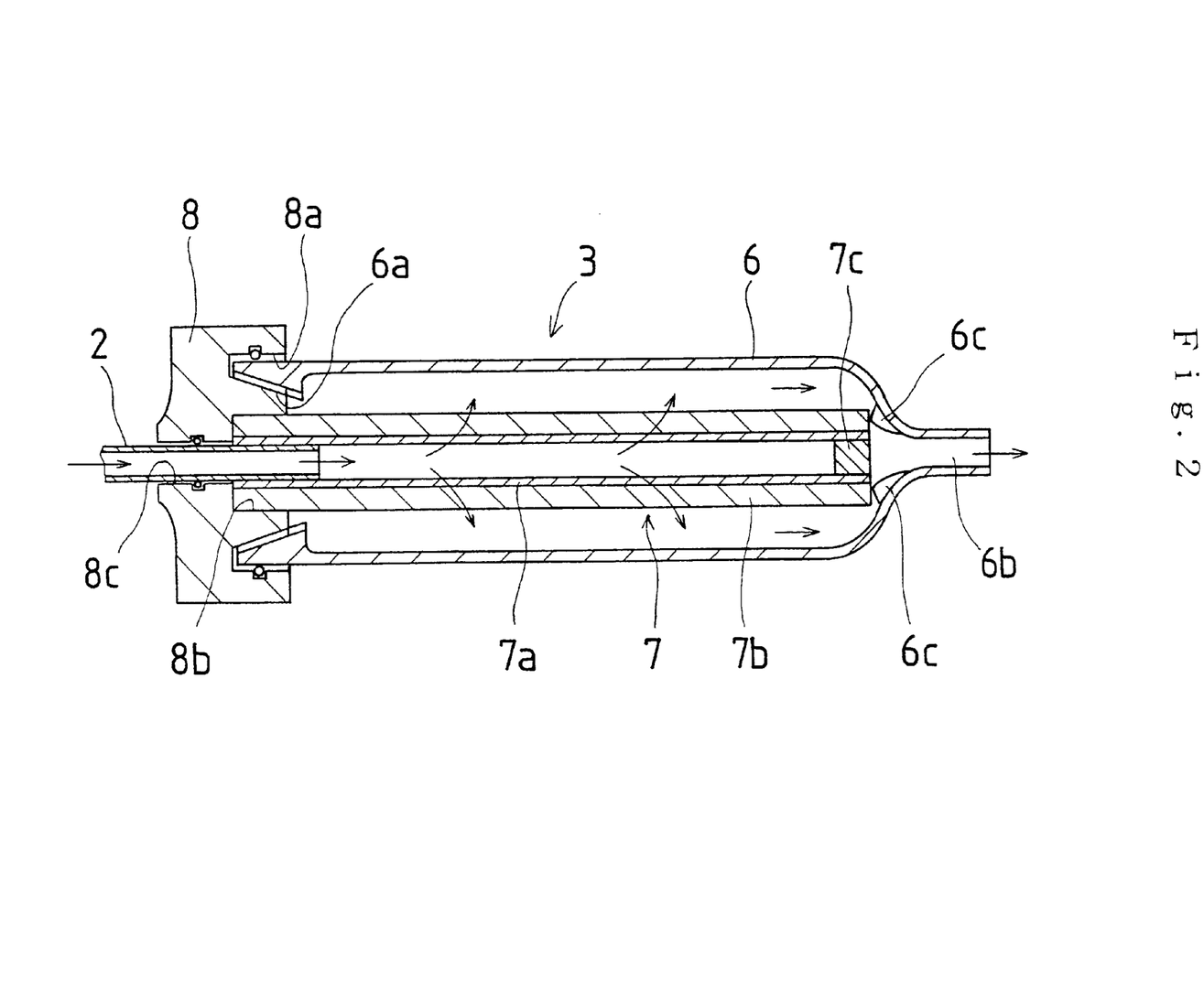
FIG. 2 is a sectional view of the collector.

As shown in FIG. 2, the collector 3 principally includes a glass vessel or housing 6, a captor 7 inserted in the housing 6 for capturing the chlorinated organic compounds, and a connector 8 for connecting the housing 6 to the sampling tube 2. The housing 6 is of a generally cylindrical shape with an opening 6a at one end thereof, and is convergent at the other end thereof which serves as an outlet port 6b. Further, the housing 6 has an abutment portion 6c provided on an interior portion thereof adjacent to the outlet port 6b for stably supporting the captor 7 within the housing 6 while allowing for passage of the gas sample.

Figure 3:
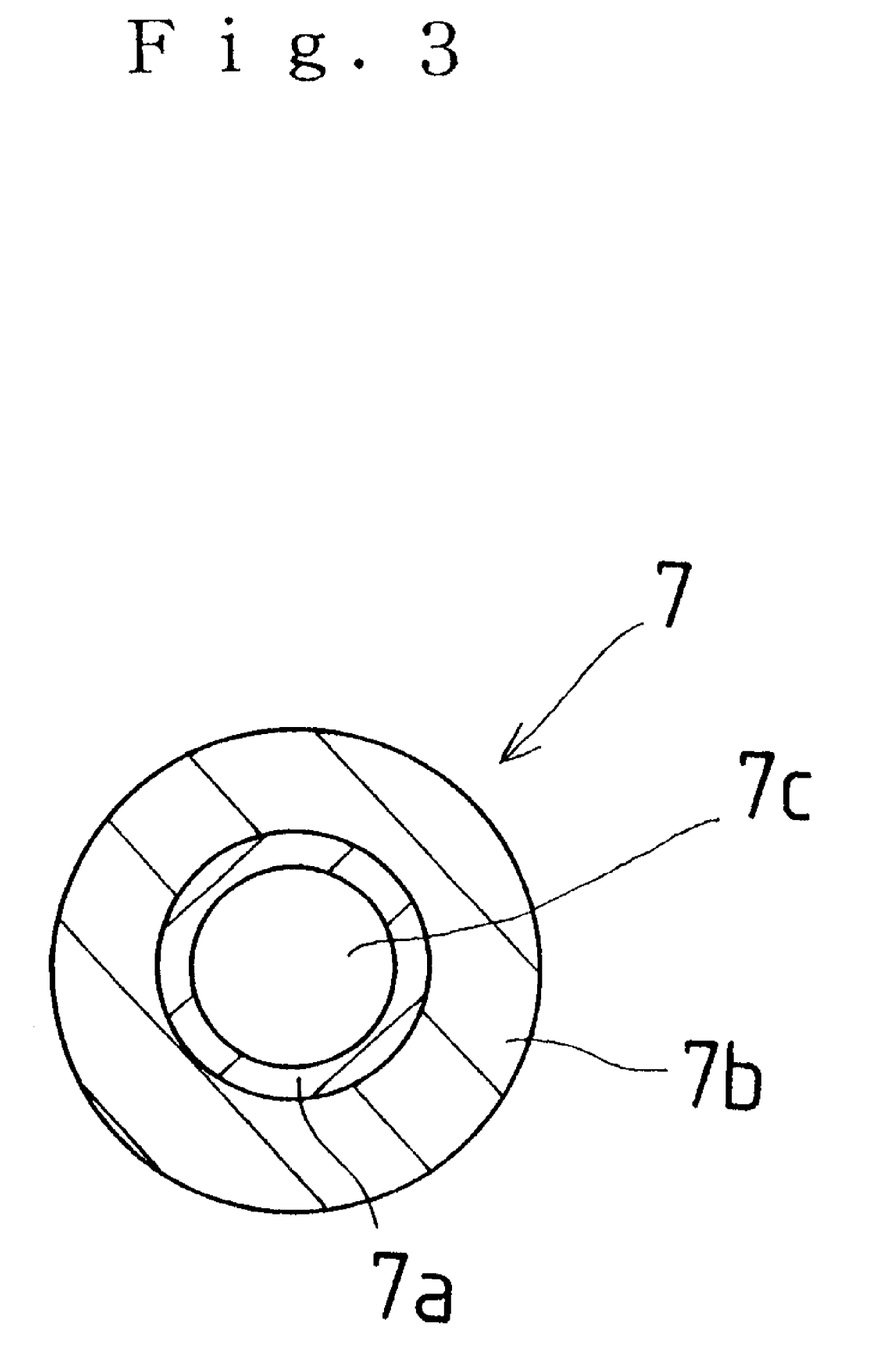
FIG. 3 is a sectional view of a captor for use in the collector, taken along a line perpendicular to an axis of the captor.

As shown in FIG. 2 and FIG. 3 (a sectional view of the captor 7 taken along a line perpendicular to an axis thereof), the captor 7 is a cylindrical member having a length of about 50 to 120 mm, and includes a gas-permeable hollow cylindrical core member 7a, a gas-permeable sheet 7b fitted around the core member 7a, and a close member 7c for closing one end of the core member 7a. The core member 7a is a porous tube, such as of a sintered glass, having fine pores in its entire body, and has an inner diameter of about 5 to 15 mm. On the other hand, the gas-permeable sheet 7b is a paper-like sheet which is composed of an adsorbent and inorganic fibers such as micro glass-fibers, and is wrapped around the core member 7a to such a thickness that the captor 7 has an outer diameter of about 10 to 20 mm.

The adsorbent to be contained in the gas-permeable sheet 7b is not particularly limited as long as it can adsorb the chlorinated organic compounds, but an example thereof is a fibrous activated carbon. The fibrous activated carbon to be herein used is not particularly limited, but typically has a specific surface area of 50 to 4,000 $m^2/g$, preferably 60 to 2,500 $m^2/g$, more preferably 70 to 2,100 $m^2/g$. If the specific surface area is less than 50 $m^2/g$, it is difficult for the gas-permeable sheet 7b to adsorb the chlorinated organic compounds (particularly, the gaseous chlorinated organic compounds). This often makes it impossible to assuredly capture the chlorinated organic compounds contained in the gas sample taken through the sampling tube 2 for removal thereof from the gas sample. If the specific surface is greater than 4,000 $m^2/g$, conversely, the strength of the fibrous activated carbon is reduced. This often makes it difficult for the gas-permeable sheet 7b to stably retain the fibrous activated carbon. Further, the adsorption of the chlorinated organic compounds by the fibrous activated carbon is enhanced to the excess, making it difficult to extract the chlorinated organic compounds captured by the captor 7 in an analyzing operation which will be described later.

Where the chlorinated organic compounds collected by the captor 7 are extracted by an inexpensive and simple ordinary extraction method such as a high speed extracting method and a Soxhlet extracting method in the analyzing operation to be described later, it is particularly preferred to use the fibrous activated carbon having a specific surface area of 70 to 2,100 $m^2/g$ as described above because the extracting operation can quickly be performed.

The aforesaid specific surface area is determined in accordance with a known method (B.E.T-B.J.H. method), for example, in which the measurement thereof is based on a nitrogen gas adsorption isotherm of an adsorbent at the boiling point of liquid nitrogen under normal pressure.

The aforesaid fibrous activated carbon is preferably contained in an amount of 0.1 to 4.0 g in the gas-permeable sheet 7b. If the amount of the fibrous activated carbon to be contained in the gas-permeable sheet 7b is less than 0.1 g, the captor 7 has a lower ability to capture the chlorinated organic compounds, so that there is a possibility that the chlorinated organic compounds in the gas sample cannot completely be captured and removed from the gas sample. If the amount of the fibrous activated carbon is greater than 4.0 g, conversely, the time required for extracting the chlorinated organic compounds from the gas-permeable sheet 7b in the chlorinated organic compound analyzing operation to be described later is increased, possibly resulting in a difficulty in quick quantitative analysis of the chlorinated organic compounds. Where a fibrous activated carbon having a specific surface area of 50 $m^2/g$ is contained in an amount of the aforesaid range in the gas-permeable sheet 7b, for example, the time required for the Soxhlet extraction is typically about 16 hours. Where the fibrous activated carbon of the same specific surface area is contained in an amount of 4.0 to 6.0 g, however, the required time increases a several-fold (e.g., about 2- to 6-fold).

The optimum range of the amount of the fibrous activated carbon to be contained in the gas-permeable sheet 7b may properly be set depending on the specific surface area of the fibrous activated carbon, i.e., the ability of the fibrous activated carbon to adsorb the chlorinated organic compounds. Where the fibrous activated carbon to be used has a smaller specific surface area thereby to have a lower ability to adsorb the chlorinated organic compounds, a relatively large amount of the fibrous activated carbon is used. Where the fibrous activated carbon to be used has a greater specific surface area thereby to have a higher ability to adsorb the chlorinated organic compounds, conversely, a relatively small amount of the fibrous activated carbon is used. With a fibrous activated carbon having a specific surface area of 70 to 400 $m^2/g$, for example, the weight of the activated carbon to be contained is preferably 2.0 to 3.5 g. With a fibrous activated carbon having a specific surface area of 600 to 800 $m^2/g$, the weight of the activated carbon to be contained is preferably 1.5 to 2.0 g. With a fibrous activated carbon having a specific surface area of 1,000 to 2,000 $m^2/g$, the weight of the activated carbon to be contained is preferably 0.8 to 1.0 g. With a fibrous activated carbon having a specific surface area of 2,500 to 3,500 $m^2/g$, the weight of the activated carbon to be contained is preferably 0.1 to 0.3 g.

The fibrous activated carbon to be used in this embodiment is not particularly limited, but examples thereof include polyacrylonitrile-based, phenol resin-based and pitch-based activated carbons.

The close member 7c is a cap such as of a fluoro-resin, which is inserted into the one end of the core member 7a to air-tightly close the end.

The aforesaid captor 7 is inserted in the housing 6 from the opening 6a, and the end thereof closed with the close member 7c is brought into abutment against the abutment portion 6c.

The connector 8 is a cylindrical member such as of a fluoro-resin, and has an outer groove 8a into which a lip of the opening 6a of the housing 6 can air-tightly be inserted, and an inner groove 8b into which an end of the captor 7 can be inserted. A through-hole 8c is formed in a central portion of the inner groove 8b. The connector 8 retains the captor 7 generally horizontally within the housing 6 via the inner groove 8b with the opening 6a of the housing 6 being air-tightly closed with the outer groove 8a. The other end portion of the sampling tube 2 air-tightly extends through the through-hole 8c so as to be inserted in the core member 7a of the captor 7.

The sucker 4 includes a gas outlet line 9 and a suction pump 10. One end of the gas outlet line 9 is connected to the outlet port 6b of the housing 6 by a tubular joint 11. The gas outlet line 9 includes a cooler 12 and a trap 13 disposed therealong in this order from the side of the collector 3. The suction pump 10 is attached to the other end of the gas outlet line 9.

An explanation will next be given to a method of using the sampling device 1, i.e., a method of collecting the chlorinated organic compounds with the use of the sampling device 1. There will herein be explained a case where a gas sample is taken for analyzing the chlorinated organic compounds such as dioxins contained in an exhaust gas flowing through a space, e.g., a flue, in an incineration plant for incineration of waste. In this case, a distal end portion of the sampling tube 2 of the sampling device 1 is inserted into a flue 14 from a sampling port 14a provided in the flue 14. At this time, a packing 15 is fitted around the sampling tube 2 to air-tightly seal a gap between the sampling tube 2 and the sampling port 14a.

When the suction pump 10 is operated in this state, a fraction of the exhaust gas flowing through the flue 14 is sucked at a constant flow rate toward the sampling device 1 to flow into the sampling tube 2. The exhaust gas flowing into the sampling tube 2 is cooled by the cooler 5 typically to a temperature of about 120° C., for example, which is lower than a dioxin generating temperature. This prevents generation of additional dioxins within the sampling tube 2.

The exhaust gas thus cooled flows into the captor 7 of the collector 3 from the sampling tube 2. The exhaust gas flowing into the captor 7 passes through the core member 7a and the gas-permeable sheet 7b, as shown by arrows in FIG. 2, and then flows toward the sucker 4 from the outlet port 6b. Soot, dust, and particulate and gaseous chlorinated organic compounds contained in the exhaust gas are simultaneously captured by the porous tube of the core member 7a and the fibrous activated carbon contained in the paper-like sheet constituting the gas-permeable sheet 7b. As a result, the soot, the dust and the chlorinated organic compounds contained in the exhaust gas are almost completely removed by the captor 7, and the exhaust gas free from the chlorinated organic compounds flows toward the sucker 4 from the outlet port 6b.

The exhaust gas discharged from the outlet port 6b flows into the gas outlet line 9, and cooled again by the cooler 12. Thus, moisture contained in the exhaust gas is condensed and trapped in the trap 13. The exhaust gas thus freed of the moisture is discharged out of the suction pump 10. The gas sampling by the sampling device 1 is carried out for a time period which is determined correspondingly to the amount of the exhaust gas to be sampled on the basis of the limit of detection of the chlorinated organic compounds (typically, an exhaust gas amount of 1 to 3 $Nm^3$/3 to 4 hours).

When the chlorinated organic compounds contained in the gas sample thus collected are to be analyzed for determination of the concentrations thereof, the sampling device 1 is removed from the flue 14, and the collector 3 is removed from the sampling device 1. At this time, the collector 3 can easily be separated from the sampling device 1 by removing the connector 8 from the opening 6a of the housing 6 and removing the tubular joint 11 from the outlet port 6b of the housing 6.

In turn, the chlorinated organic compounds adhering onto the interior of the sampling tube 2 are rinsed off with a solvent for extraction thereof, and the chlorinated organic compounds adsorbed by the captor 7 of the collector 3 are extracted with a solvent. The extracting operation for extraction of the chlorinated organic compounds from the captor 7 may be carried out, for example, with the use of an ordinary Soxhlet extractor. However, quick extraction can be achieved with the use of a high speed extractor, since the captor 7 which has a small size as mentioned above can be accommodated in a cell of the high speed extractor. The adsorbed chlorinated organic compounds can quickly be eluted into the solvent in a short time with no need for special extraction conditions for reduction of the extraction time, because the amount of the fibrous activated carbon contained in the gas-permeable sheet 7b of the captor 7 is set within the aforesaid range.

In the analysis of the chlorinated organic compounds, the extracts obtained in the aforesaid manner are collectively subjected to an analyzing operation. The analyzing operation may be performed, for example, by a gas chromatography/mass-spectrometric analysis (GC/MS) in accordance with "Manual of Standard Measurement and Analysis of Dioxins in Refuse Dump" compiled by Environmental Maintenance Section, Water Supply and Environmental Sanitation Department, Environmental Health Bureau, Ministry of Health and Welfare, Japan, and published by the Foundation of Waste Research Institute in March, 1997.

When the next gas sample is to be obtained with the use of the sampling device 1, the collector 3 is replaced with a new one. Since the sampling device 1 can be used for the next gas sampling by sufficiently cleaning only the sampling tube 2, the preparatory operation to be performed prior to the gas sampling is remarkably facilitated as compared with the conventional case, thereby drastically reducing the time required for the gas sampling. Further, the sampling device 1 is simpler in construction, and easier to handle and transport than the conventional complicated sampling device.

The chlorinated organic compound collector according to the present invention can be modified as follows:

(1) Although the porous tube constituting the core member 7a of the captor 7 is composed of the sintered glass in the aforesaid embodiment, the present invention can be implemented as well with the porous tube being composed of a quartz glass. Further, a gas-permeable porous tube composed of any of various materials such as ceramics may be used instead of the glass porous tube for implementation of the invention.

(2) In the aforesaid embodiment, the paper-like sheet comprising the fibrous activated carbon and the inorganic fibers (micro glass-fibers) is used as the gas-permeable sheet 7b for the captor 7 of the collector 3, but the arrangement of the gas-permeable sheet 7b according to the present invention is not limited thereto For example, the present invention can be implemented as well by using a paper-like sheet comprising a fibrous activated carbon, natural fibers and a synthetic resin. The fibrous activated carbon to be herein used may be the same as that used in the aforesaid embodiment, and the amount of the fibrous activated carbon to be contained in the gas-permeable sheet can be the same as in the aforesaid embodiment.

(3) Although the aforesaid embodiment employs as the captor 7 of the collector 3 the cylindrical core member 7a wrapped with the gas-permeable sheet 7b containing the fibrous activated carbon, the arrangement of the captor 7 according to the invention is not limited thereto. For example, a cylindrical captor formed by rolling a gas-permeable sheet 7b as used in the aforesaid embodiment, i.e., a paper-like sheet comprising the fibrous activated carbon and the inorganic fibers (e.g., micro glass-fibers) and closing one end of the resulting roll may be used instead of the captor 7 for implementation of the invention. Where such a captor is used, the particulate and gaseous chlorinated organic compounds contained in an exhaust gas are simultaneously captured and removed from the exhaust gas by the fibrous activated carbon and the inorganic fibers which constitute the captor.

Figure 4:
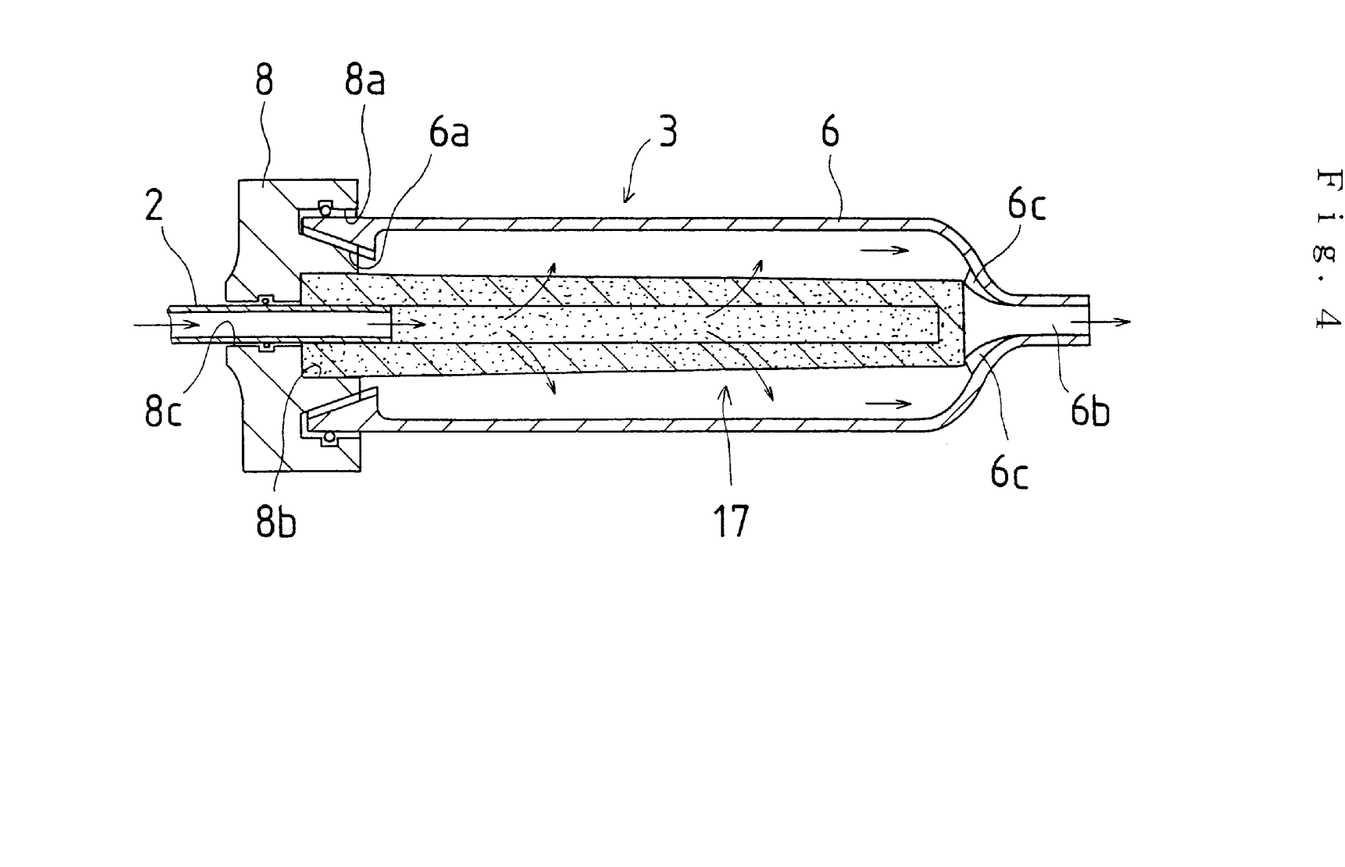
FIG. 4 is sectional view illustrating a collector which employs a captor according to another embodiment.
Figure 5:
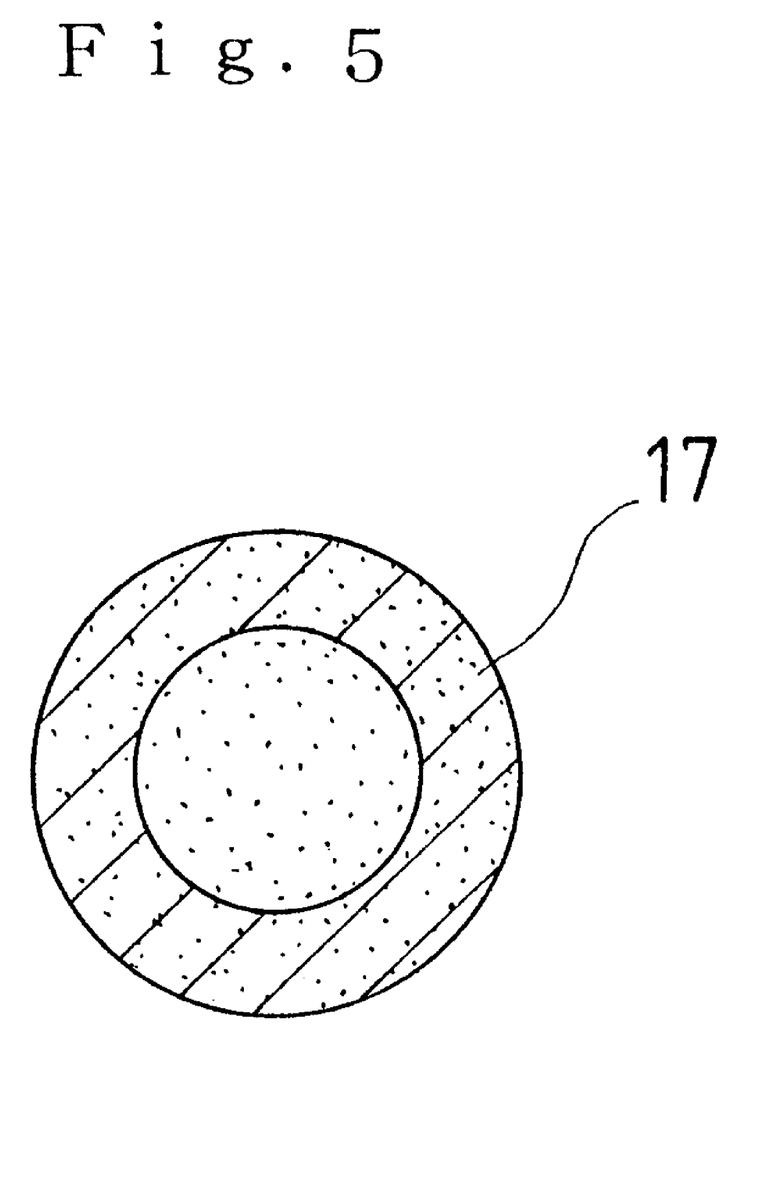
FIG. 5 is a sectional view of the captor according to the another embodiment, taken along a line perpendicular to an axis of the captor.

The paper-like sheet according to the modified embodiment (2) may also be used for the captor of this arrangement.
(4) Although the paper-like sheet is used as the gas-permeable sheet 7b in the embodiments described above, the gas-permeable sheet 7b may be a felt sheet or a laminate sheet composed of the same materials as the paper-like sheet.
(5) FIG. 4 illustrates a collector which includes another captor instead of the captor 7 used in the aforesaid embodiment. In FIG. 4, the collector 3 has substantially the same construction as in the aforesaid embodiment except the captor 17 and, therefore, like components are denoted by like reference numerals as used in the aforesaid embodiment. The captor 17 is a generally cylindrical gas-permeable molded member with one end thereof being open and with the other end thereof (adjacent to the abutment portion 6c) being closed (see FIG. 5 which is a sectional view of the captor 17 taken along a line perpendicular to an axis thereof). This molded member is obtained by molding a mixture of a fibrous activated carbon, inorganic fibers and a binder, and has a tapered shape with the closed end having a smaller outer diameter than the open end. Usable as the fibrous activated carbon and the inorganic fibers are those used in the aforesaid embodiment. An example of the binder to be used is a cellulose binder. The amount of the fibrous activated carbon to be contained in the molded member can be the same as in the aforesaid embodiment.

The captor 17 is disposed within the housing 6, like the captor 7 used in the collector 3 according to the aforesaid embodiment. More specifically, the captor 17 is inserted into the housing 6 with the closed end abutting against the abutment portion 6c, and an end portion of the sampling tube 2 is inserted in the open end. In the collector 3 which employs the captor 17, an exhaust gas from the sampling tube 2 passes through the captor 17, and then flows toward the sucker 4 from the outlet port 6b. At this time, soot, dust, and particulate and gaseous chlorinated organic compounds contained in the exhaust gas are removed simultaneously by the inorganic fibers and the fibrous activated carbon constituting the captor 17, and the exhaust gas free from the chlorinated organic compounds flows toward the sucker 4 from the outlet port 6b. As a result, the particulate and gaseous chlorinated organic compounds contained in the exhaust gas are collected by the captor
(6) Various captors besides those according to the modified embodiments may be used instead of the captor 7 used in the aforesaid embodiment. For example, ① cylindrical filter-paper-like member containing a fibrous activated carbon and ② a laminate of a porous glass plate (e.g., disk) and a gas-permeable sheet containing a fibrous activated carbon may be used. The kind and amount of the fibrous activated carbon to be used are the same as in the aforesaid embodiment.
(7) Although the embodiments described above employ the fibrous activated carbon as the adsorbent, the invention can be implemented as well by employing any of various kinds of granular activated carbons as the adsorbent. The granular activated carbons usable in the present invention are, for example, those having a specific surface area equivalent to the fibrous activated carbon used in the embodiments. Where the captor according to any of the aforesaid embodiments is constructed with the use of such a granular activated carbon, the amount of the granular activated carbon to be contained is preferably the same as in the aforesaid embodiments.

A cylindrical porous tube such as of a quartz glass or a sintered glass which has a closed end and is filled with the granular activated carbon may be used instead of the captor 7 used in the aforesaid embodiment for implementation of the invention.
(8) Although the embodiments described above employ either the fibrous activated or the granular activated carbon, the fibrous activated carbon and the granular activated carbon may be used in combination for implementation of the invention. In this case, the amount of the activated carbon, i.e., the total amount of the fibrous activated carbon and the granular activated carbon, is preferably the same as in the embodiments.
(9) Although the embodiments described above are directed to the collection of the chlorinated organic compounds such as dioxins contained in an exhaust gas emitted from an incinerator for incineration of waste, the collector and the sampling method according to the present invention may be used to sample any other fluids than the exhaust gas for the collection of the chlorinated organic compounds contained therein. For example, the collector and the sampling method using the same in accordance with the present invention are applicable to collection of the chlorinated organic compound contained in ambient air, or in water such as industrial waste water, see water, fresh water, tap water or the like.

The present invention will hereinafter be described in greater detail by way of examples thereof.

EXAMPLE 1

A captor 7 according to the aforesaid embodiment was fabricated by using a gas-permeable sheet which contained 1.5 g of a coal-pitch-based fibrous activated carbon having a specific surface area of 700 $m^2/g$, and a sampling device 1 was prepared by using the captor thus fabricated. The captor had an inner diameter of 12 mm, an outer diameter of 19 mm and a length of 120 mm.

With the use of the sampling device, a gas sample was taken from a flue in an incineration plant during incineration of waste. The gas sampling was carried out in accordance with above-mentioned "Manual of Standard Measurement and Analysis of Dioxins in Refuse Dump". The chlorinated organic compounds (dioxins) collected by the sampling device were quantitatively analyzed. The result of the quantitative analysis virtually matched with the result of the quantitative analysis of chlorinated organic compounds in a sample taken from the same flue with the use of the conventional sampling device specified in "Manual of Standard Measurement and Analysis of Dioxins in Refuse Dump". Thus, it is confirmed that the sampling device of Example 1 was able to collect the chlorinated organic compounds contained in the gas sample with the same level of reliability as the conventional sampling device.

EXAMPLE 2

A gas-permeable paper-like sheet which contained 0.8 g of a coal-pitch-based fibrous activated carbon having a specific surface area of 1,000 m²/g and micro glass-fibers as the inorganic fibers was rolled into a roll having an inner diameter of 15 mm, an outer diameter of 17 mm and a length of 120 mm, and one end of the resulting roll was closed for fabrication of a captor according to the aforesaid modified embodiment (3). A sampling device was produced in substantially the same manner as in Example 1, except that the captor thus fabricated was used instead of the captor used in Example 1. When the chlorinated organic compounds (dioxins) collected with the use of the sampling device thus produced were quantitatively analyzed in the same manner as in Example 1, substantially the same result as in Example 1 was obtained.

EXAMPLE 3

Micro glass-fibers and a coal-pitch-based fibrous activated carbon having a specific surface area of 100 m²/g were properly blended, to which a cellulose binder was added as the binder component, and the resulting mixture was molded for fabrication of a captor 17 in accordance with the aforesaid modified embodiment (5), which contained 3.0 g of the fibrous activated carbon and had an outer diameter of an open end of 19 mm, an outer diameter of a closed end of 18 mm, a wall thickness of 5 mm and a length of 120 mm. A sampling device was produced in substantially the same manner as in Example 1, except that the captor thus fabricated was used instead of the captor used in Example 1. When the chlorinated organic compounds (dioxins) collected with the use of the sampling device thus produced were quantitatively analyzed in the same manner as in Example 1, substantially the same result as in Example 1 was obtained.

EXAMPLE 4

Micro glass-fibers and a coal-pitch-based fibrous activated carbon having a specific surface area of 1,000 m²/g were properly blended, to which a cellulose binder was added as the binder component, and the resulting mixture was molded for fabrication of a captor 17 in accordance with the aforesaid modified embodiment (5), which contained 1.0 g of the fibrous activated carbon and had an outer diameter of an open end of 19 mm, an outer diameter of a closed end of 18 mm, a wall thickness of 5 mm and a length of 60 mm. A sampling device was produced in substantially the same manner as in Example 1, except that the captor thus fabricated was used instead of the captor used in Example 1. When the chlorinated organic compounds (dioxins) collected with the use of the sampling device thus produced were quantitatively analyzed in the same manner as in Example 1, substantially the same result as in Example 1 was obtained.

The present invention can be embodied in any of various ways without departing from the spirit and principal features of the invention. Therefore, the embodiments described above are merely illustrative but not limitative of the invention in any aspects. The scope of the invention is, in no way, limited by the description in the specification, but defined by the following claims. Further, any modifications and alterations made within the range of equivalents to the claims of the invention are deemed to fall within the scope of the invention.

What is claimed is:

1. A chlorinated organic compound collector for collecting chlorinated organic compounds contained in a fluid, the collector comprising:
   a vessel which permits passage of the fluid therethrough; and
   a molded captor disposed within the vessel for simultaneously capturing particulate and gaseous chlorinated organic compounds contained in the fluid for removal thereof from the fluid.

2. A chlorinated organic compound collector as set forth in claim 1, wherein the captor includes an adsorbent capable of adsorbing the chlorinated organic compounds.

3. A chlorinated organic compound collector as set forth in claim 2, wherein the adsorbent is an activated carbon.

4. A chlorinated organic compound collector as set forth in claim 3, wherein the activated carbon is at least one of a granular activated carbon and a fibrous activated carbon.

5. A chlorinated organic compound collector as set forth in claim 4, wherein the activated carbon has a specific surface area of 50 to 4,000 m²/g.

6. A chlorinated organic compound collector as set forth in claim 5, wherein the activated carbon is present in an amount of 0.1 to 4.0 g in the captor.

7. A chlorinated organic compound collector as set forth in claim 1, wherein the captor is a hollow cylindrical member which is formed from a gas-permeable paper-like sheet comprising inorganic fibers and an adsorbent capable of adsorbing the chlorinated organic compounds and has a closed end.

8. A chlorinated organic compound collector as set forth in claim 7, wherein the adsorbent is an activated carbon.

9. A chlorinated organic compound collector as set forth in claim 8, wherein the activated carbon is at least one of a granular activated carbon and a fibrous activated carbon.

10. A chlorinated organic compound collector as set forth in claim 9, wherein the activated carbon has a specific surface area of 50 to 4,000 m²/g.

11. A chlorinated organic compound collector as set forth in claim 10, wherein the activated carbon is present in an amount of 0.1 to 4.0 g in the hollow cylindrical member.

12. A chlorinated organic compound collector as set forth in claim 1, wherein the captor is a gas-permeable hollow cylindrical molded member which comprises inorganic fibers and an adsorbent capable of adsorbing the chlorinated organic compounds and has a closed end.

13. A chlorinated organic compound collector as set forth in claim 12, wherein the adsorbent is an activated carbon.

14. A chlorinated organic compound collector as set forth in claim 13, wherein the activated carbon is at least one of a granular activated carbon and a fibrous activated carbon.

15. A chlorinated organic compound collector as set forth in claim 14, wherein the activated carbon has a specific surface area of 50 to 4,000 m²/g.

16. A chlorinated organic compound collector as set forth in claim 15, wherein the activated carbon is present in an amount of 0.1 to 4.0 g in the hollow cylindrical molded member.

17. A chlorinated organic compound collector for collecting chlorinated organic compounds contained in a fluid, the collector comprising:
    a vessel which permits passage of the fluid therethrough; and
    a captor disposed within the vessel for simultaneously capturing particulate and gaseous chlorinated organic compounds contained in the fluid for removal thereof from the fluid,
    wherein the captor includes a gas-permeable tube having a closed end, and a gas-permeable sheet fitted around the gas-permeable tube, wherein the gas-permeable sheet contains an adsorbent capable of adsorbing the chlorinated organic compounds.

18. A chlorinated organic compound collector as set forth in claim 17, wherein the gas-permeable tube is a porous tube.

19. A chlorinated organic compound collector as set forth in claim 17, wherein the gas-permeable sheet is a paper-like sheet comprising the adsorbent and inorganic fibers.

20. A chlorinated organic compound collector as set forth in claim 19, wherein the adsorbent is an activated carbon.

21. A chlorinated organic compound collector as set forth in claim 20, wherein the activated carbon is at least one of a granular activated carbon and a fibrous activated carbon.

22. A chlorinated organic compound collector as set forth in claim 21, wherein the activated carbon has a specific surface area of 50 to 4,000 $m^2/g$.

23. A chlorinated organic compound collector as set forth in claim 22, wherein the activated carbon is present in an amount of 0.1 to 4.0 g in the gas-permeable sheet.

24. A chlorinated organic compound collecting method for collecting chlorinated organic compounds contained in a fluid, comprising the step of capturing particulate and gaseous chlorinated organic compounds contained in the fluid for removal thereof from the fluid with the use of a molded captor capable of simultaneously capturing both particulate and gaseous chlorinated compounds.

* * * * *